United States Patent [19]

Laurence et al.

[11] Patent Number: 4,844,892

[45] Date of Patent: Jul. 4, 1989

[54] PHEROMONES

[75] Inventors: Brian R. Laurence, London; John A. Pickett, Kimpton, both of England

[73] Assignee: National Research Development Corporation, England

[21] Appl. No.: 257,956

[22] Filed: Oct. 14, 1988

Related U.S. Application Data

[62] Division of Ser. No. 503,139, Jun. 8, 1983, Pat. No. 4,803,289.

[30] Foreign Application Priority Data

Oct. 27, 1981 [GB] United Kingdom ............... 8132367
Oct. 22, 1982 [WO] PCT Int'l Appl. ... PCT/GB82/00301

[51] Int. Cl.⁴ ..................... A01N 25/00; A01N 43/16
[52] U.S. Cl. ..................................... 424/84; 514/460
[58] Field of Search ........................... 514/460; 424/84

[56] References Cited

PUBLICATIONS

Starratt, "Synthesis of Erythro-5,6-diacetoxyhexadecanoic Acid, a Novel Fatty Acid from Mosquito Eggs", *Chemistry and Physics of Lipids*, vol. 16, pp. 215–218 (1976).

Starratt et al., "An Oviposition Pheromone of the Mosquito Culex Tarsalis: Diglyceride Composition of the Active Fraction", *Biochemica et Biophysica Acta*, vol. 280, pp. 187–193 (1972).

Fore et al., "Some Derivatives of 5-Eicosenoic Acid", *J. Am. Oil Chemists Soc.*, vol. 43 (10), pp. 581–584 (1966).

Ikeshoji et al., "Attractancy and Repellency of Alkyl Carbonyl Compounds for Mosquito Oviposition", *Jap J. Sanit. Zool*, vol. 25 (1), pp. 89–94 (1974).

Chemical Abstracts, 80:95622t.

*Primary Examiner*—Allen J. Robinson
*Attorney, Agent, or Firm*—Jacobs & Jacobs

[57] ABSTRACT

Compounds of formula

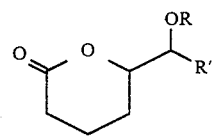

in which R represents hydrogen, formyl or an alkanoyl group of two to twenty-five carbon atoms and R' represents an alkyl group of one to thirty-five carbon atoms are of value as mosquito attractants, mosquitoes being attracted to a location where they and/or their eggs or larvae are then destroyed.

35 Claims, No Drawings

PHEROMONES

CROSS REFERENCE

This is a division of Ser. No. 503,139, now U.S. Pat. No. 4,803,289, filed June 8, 1983.

This invention relates to compounds having activity as oviposition attractants for mosquitoes and to the use of these compounds in mosquito control.

The eggs of the mosquitoes *Culex pipiens fatigans* (=*quinquefasciatus*), *Culex pipiens pipiens*, *Culex pipiens molestus* and *Culex tarsalis* have previously been studied with a view to identification of the natural oviposition attractant which is present therein. The eggs have been found to contain a mixture of 1,3-diglycerides of mono- and di-acetoxy fatty acids and these glycerides have been identified as being responsible for the natural oviposition attractive effect of the eggs. These compounds are of interest in mosquito control in view of the involvement of mosquitoes of this genus in various parts of the world in the spread of various diseases, for example *Culex pipiens fatigans* acting as a vector for filarial disease (*Wuchereria bancrofti*) known as elephantiasis, *Culex tarsalis* for Western equine encephalitis, the *Culex tritaeniorhynchus* group for Japanese B encephalitis and other viral diseases, and the *Culex pipiens* group for Rift Valley fever.

We have now isolated from the apical droplets of eggs of *Culex pipiens fatigans* further, non-glyceride, oviposition attractants having a structure which is an unusual one among pheromones. These attractants, whose existence was previously quite unexpected, are present in the apical droplet of the eggs in only small amounts but they are significantly more potent as oviposition attractants for mosquitoes of this general type than the previously reported glyceride oviposition attractants. These newly discovered compounds, together with certain analogues thereof, are therefore of considerable interest for use in mosquito control.

Accordingly, the present invention comprises a compound of formula

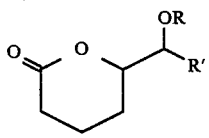

(I)

in which R represents hydrogen, formyl or an alkanoyl (alkyl-CO—) group of two to twenty-five carbon atoms and R' represents an alkyl group of one to thirty-five carbon atoms.

The major naturally occurring compound of this type is 6-acetoxy-5-hexadecanolide but we have also identified the compounds 6-hydroxy-5-hexadecanolide and 6-acetoxy-5-tetradecanolide as occurring in moquito eggs. However, whilst compounds (I) in which R is hydrogen or especially an acetyl group are of particular interest, as are compounds (I) in which R' is n-octyl or particularly n-decyl, variations from the naturally occurring structures through the presence of a formyl group or of other branched or, more preferably, straight chain alkanoyl or alkyl groups, for example propionyl in the case of R and n-hexyl or n-dodecyl in the case of R', are also of interest. In particular, the presence of a smaller alkyl group R', for example of as few as six, four or even less carbon atoms, may be of value in some circumstances through the consequent increase in volatility of the compound (I). Similarly, the presence of an alkyl group R' larger than $C_8$–$C_{10}$ or an alkanoyl group R larger than $C_2$ may be of value in the preparation of long acting compositions through the consequent decrease in volatility. Such higher molecular weight compounds may also be advantageous through a consequent reduction in water solubility, although 6-acetoxy-5-hexadecanolide itself already has only a low water solubility. An increase in the molecular weight of the compound through an increase in the size of R' rather than of R is preferred in view of the lesser effect upon the oviposition attractant activity of the compound. Thus, a molecular weight of about 600 may conveniently be achieved through an increase in the size of R' by about twenty carbon atoms rather than of R or of both R and R' by about ten carbon atoms. Accordingly a preferred upper limit of size for an alkanoyl group comprising R is less than twenty-five or even twenty carbon atoms, an upper limit of ten carbon atoms or more especially only three, four or five carbon atoms being preferred, whilst an increase in the size of an alkyl group comprising R' not only to fourteen, sixteen or eighteen carbon atoms, but also to twenty, twenty-five or thirty carbon atoms, may be more readily accepted.

6-Acetoxy-5-hexadecanolide occurs naturally in the erythro form and accordingly compounds (I) having an erythro configuration are of rather greater interest than those of the threo configuration. It will be appreciated that compounds of both the erythro and the threo configuration may exist in optically active forms and that one of the d(+) or l(−) isomers may be of particular interest by virtue of its possession of an enhanced property, particularly biological activity, as compared with the other or with the racemic, dl, mixture. However, it is of interest that, somewhat unusually, the racemic mixture itself shows a high level of activity.

Specific compounds according to the present invention, in increasing order of interest, are 6-hydroxy-5-tetradecanolide, 6-acetoxy-5-tetradecanolide, 6-hydroxy-5-hexadecanolide and 6-acetoxy-5-hexadecanolide. The d- and l-erythro isomers of the last mentioned compound have the structures shown below (Ac representing acetyl)

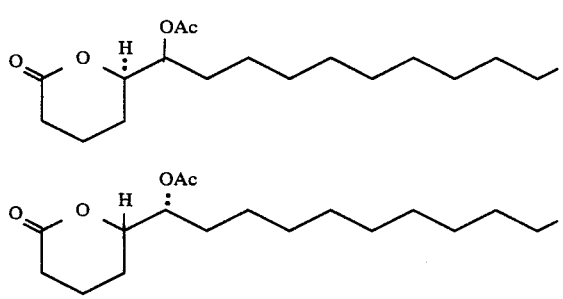

Although certain of the compounds (I) occur naturally, it is preferred to prepare the compounds synthetically for use as oviposition attractants. Compounds in which R is hydrogen and those in which R is a formyl or other acyl group may each conveniently be prepared from a compound of formula

$$HO_2C—(CH_2)_3—CH(OH)—CH(OH)—R' \qquad (II)$$

as a precursor. When R is hydrogen such a precursor may be treated with a strong inorganic acid such as hydrochloric acid, and then extracted into an organic solvent, to effect formation of the δ-lactone having a hydroxy group adjacent to the ring. Compounds having R=H may, however, be obtained in admixture with the corresponding open chain dihydroxy compound (II). When R is acyl, the appropriate anhydride (RCO)$_2$O or acid chloride RCOCl may be used, for example in the presence of an organic base such as dry pyridine in the case of the anhydride, to effect formation of the δ-lactone having an acyloxy group adjacent to the ring, or, where R is a higher acyl group than acetyl, acetic anhydride may be used initially and acidolysis may then be employed to modify the resulting acetoxy group. Such acidolysis may conveniently be effected by heating the acetoxy compound with a higher molecular weight acid, an appropriate catalyst such as p-toluene sulphonic acid being used where desirable. Alternatively, compounds (I) in which R is acyl may be prepared by the esterification of the corresponding compound in which R is hydrogen and compounds (I) in which R is hydrogen may be prepared by the hydrolysis of the corresponding compound in which R is acyl, the lactone ring being re-formed, if opened by hydrolysis under basic conditions, through treatment with strong acid.

A compound (I) of the erythro or threo configuration may be prepared by the use of a precursor having the appropriate configuration. For instance, the erythro or threo dihydroxy acid (II) may be used, this conveniently being obtained by hydroxylation under suitable conditions of the appropriate (Z) or (E) unsaturated acid. Thus, the erythro isomer may be obtained by the cis hydroxylation, for example with potassium permanganate, of the (Z) unsaturated or by the trans hydroxylation, for example with hydrogen peroxide, of the (E) unsaturated acid. If a d or l isomer is required, substantially free from the other of these isomers, a resolution step must be introduced into the synthesis and conveniently such a resolution may be effected using a compound of formula (I) rather than a precursor such as a compound of formula (II). One convenient approach involves the preparation of a diastereoisomeric mixture from the substantially pure erythro or threo form of the compound (I) in which the appropriate group R' is present but which has a group R which is hydrogen. Such a mixture may be readily obtained by treatment of this compound (I) with a pure isomer of an optically active esterifying agent such as l- or particularly d-α-methoxy-α-trifluoromethylphenylacetyl chloride. The diastereoisomers may then be separated, for example by thin layer chromatography or high pressure liquid chromatography, and the appropriate isomer then hydrolysed to yield the required d or l compound (I) in which R is hydrogen and which may then be esterified where the desired compound (I) has a group R which is acyl. An alternative approach involves the acidolysis of a compound (I) in which R is acetyl by treatment with a pure isomer of an optically active acid such as l- or particularly d-α-methoxy-α-trifluoromethylphenylacetic acid to give a diastereoisomeric mixture which may be similarly separated. Acidolysis will then yield the required d or l optically pure compound (I) in which R is acyl.

It will be appreciated that whether the compounds (I) are obtained by isolation from nature or, more preferably, synthetically, they are conveniently prepared in substantially pure form, i.e. substantially free from by-products of manufacture not having the formula (I) shown hereinbefore. Although the compounds (I) may be used in the present invention in the form of a composition containing more than one such compound in which R and/or R' may differ, for example as a mixture of two or more of the three naturally occurring compounds (I) referred to hereinbefore, it is in practice preferable for the compounds (I) initially to be prepared substantially free even from by-products of manufacture of a different formula (I) and for any mixture which is used to be produced by the deliberate mixing of selected proportions of different compounds (I). The use of a mixture of stereoisomers of a compound of a particular formula (I) will often be acceptable, although as indicated previously, it may in some circumstances be worthwhile preparing the compound in its erythro or threo form, which may conveniently be substantially free from the other such form, or even as the optically active d or l isomer of one of such forms, which may conveniently be substantially free from the other such optically active isomer. The words "substantially free from" have been used herein particularly to indicate a purity of 90% or more by weight.

Alternative approaches which may be considered for the preparation of a synthetic compound (I) for use as an oviposition attractant are the in situ preparation of the compound from a precursor thereof, for example the use of a dihydroxy acid (II), an ester thereof formed at the carboxyl group, or a diglyceride of such compounds, which compound is cyclised in situ, conveniently by microbiological action or chemical, including enzymic, action. The deliberate preparation of the compounds by microbiological action does of course constitute synthetic preparation equally with chemical synthesis.

Moreover, it will be appreciated that the compounds described herein may also be prepared by other procedures than those described, particularly by other procedures described in the art for the preparation of related compounds of a similar type.

The value of compounds according to the present invention lies in their use in the attraction of mosquitoes of the genus Culex, particularly gravid female mosquitoes, and also of certain other genera, especially those related genera of egg raft laying mosquitoes. Such mosquitoes are conveniently attracted to particular sites which are further treated either concommitantly or subsequently to kill the young mosquitoes in the egg or larval form and/or, more particularly, to kill the adult, particularly adult female, mosquitoes. Mosquitoes generally lay their eggs on water and the compounds are therefore conveniently applied in the vicinity of or preferably directly on the surface of areas of water where the mosquitoes may be expected to breed naturally, for example water in proximity to human habitation such as is present in artificial containers, tanks, drains, cess pits etc., or alternatively to artificially created areas of water, for example water contained in conveniently positioned receptacles. This method may be applied with particular advantage to domestic habitats where there is close association between the disease vector and man. The invention thus includes a method for use in mosquito control which comprises applying a compound (I) as defined above to a location for the purpose of attracting mosquitoes to that location, mosquitoes attracted thereto by the compound (I) and/or their eggs or larvae then being destroyed.

For use as described above, the compounds (I) may be formulated in various ways and the invention includes a mosquito attractant composition comprising a compound (I) as defined above together with a suitable diluent or carrier. Such compositions may consist of an oil based formulation or an aqueous formulation, which latter may conveniently contain a suitable amount, for example up to about 20%, particularly about 10%, by volume of an emulsifying agent, especially a non-ionic surface active agent which may conveniently be one based on a polyether structure, for example polyoxyethylene stearate or nonylphenylpolyethoxyethanol. The use of a surface active agent will promote contact of the composition with the site to which it is applied but care should be taken to avoid unduly solubilising the compound (I). Other components may also be included in the composition and, although many of the compounds (I) have a very low solubility in water, it may be advantageous to include an agent such as a silicone oil in the composition to further prevent mixing of the composition with the water usually present at the location to which it is applied. Techniques such as electrostatic spraying may of course be used for applying the composition, where appropriate, and may even enable the compound (I) to be applied without the addition of a diluent or carrier. The compounds may also be applied in monolayers or by the use of various other techniques known in the art, for example in microencapsulated form. Formulations for domestic use, for example as aerosols, are also of some interest.

Although the mosquitoes, once attracted, may be destroyed by physical means, for example by trapping at the location to which the compound (I) is applied, it is often more convenient to use some form of insecticidal agent to destroy the eggs, larvae or adult mosquitoes. A wide variety of agents may be used for this purpose either in the bulk of water at the site of application or on the surface thereof, including inorganic poisons and even the production of a high salt level in the water. Organic pesticides are, however, of especial interest, particularly pyrethroid pesticides, for example permethrin, organophosphorus pesticides, for example malathion or fenitrothion and some carbamates, for example carbaryl, etc. Compounds of particular value as ovicides or larvicides, such as chlorpyrifos, temephos, diflubenzuran, chlorodimeform, growth regulators such as methoprene and dimilin, phathogenic organisms, such as *Bacillus thuringensis*, or their toxins, larvicidal pellets, dusts and oils may be utilized alone or together with insecticides such as those described above which are of particular value for use against adult mosquitoes. The insecticides may be applied subsequently to the attractant compound (I) in a separate procedure but it is particularly convenient for the insecticide or insecticides to be applied together with this compound. An especially convenient aspect of the present invention consists of a mosquito control composition comprising as active components thereof a compound (I) as defined above together with an insecticide.

Whilst quantitative details of the use of the compounds (I) will depend on various factors, not least the particular compound (I) employed, it is an indication of the level of activity of these compounds that in laboratory tests synthetic 6-acetoxy-5-hexadecanolide has been shown to act as an attractant for gravid Culex mosquitoes at levels as low as the equivalent of one sixteenth of an egg raft (i.e. at a level of 0.02 $\mu$g, each *Culex pipiens fatigans* egg raft containing only about 0.3 $\mu$g of 6-acetoxy-5-hexadecanolide) and such activity has been found to be maintained over a range of up to about four hundred times this level. Such a wide range indicates considerable latitude with regard to the critical dosage required in the field. In practice, however, although activity at very low levels has been observed in the laboratory, it may be desirable to use a larger amount of 6-acetoxy-5-hexadecanolide, or of the equivalent amount of another compound (I), for example an amount of as much as 25, 50 or 100 micrograms or even more being applied per week to a particular site with due attention being given to the size of a site, so that a natural site containing a large surface area of water will require more compound than a smaller artificial receptacle.

The invention is illustrated by the following examples.

EXAMPLE 1

Isolation from the Apical Droplets of Mosquito Eggs of 6-Acetoxy-5-hexadecanolide, 6-Hydroxy-5-hexadecanolide and 6-Acetoxy-5-tetradecanolide Apical droplets are removed on fine glass rods from eggs of *Culex pipiens fatigans* and are dissolved in hexane. Examination of the volatile components present in this extract using gas chromatography/mass spectrometry [Flexsil capillary column, 25 m×0.2 mm, OV101, 50° C. (10 minutes) 4° C./minute 200° C., He 1 ml/min, directly coupled to m.s. electron impact, 70 eV, 200° C. shows a major peak ($R_t$ 64 minutes, relative ion current 100)] together with other peaks including a peak of $R_t$ 59 minutes with a relative ion current of 25 and a peak of $R_t$ 53 minutes with a relative ion current of 20. The compounds of $R_t$ 64, 59 and 53 minutes are, respectively, 6-acetoxy-5-hexadecanolide, 6-hydroxy-5-hexadecanolide and 6-acetoxy-5-tetradecanolide.

Thin layer chromatography of the hexane solution on silica gel 60 (0.25 mm) with ether gives a series of spots detectable in control with iodine vapour. The material from the $R_f$ 0.39 region of the plate is removed and the silica gel extracted with ether. Evaporation of the solution gives a residue of erythro-6-acetoxy-5-hexadecanolide together with some lower $R_t$ components including 6-acetoxy-5-tetradecanolide.

In order to obtain the three compounds in substantially pure form preparative thin layer chromatography is used to separate the two acetoxy compounds from the hydroxy compound and/or preparative gas liquid chromatography is used to separate the two acetoxy compounds (and also the hydroxy compound). The yield of erythro-6-acetoxy-5-hexadecanolide obtained is about 0.3 micrograms per egg raft. The compound isolated from the natural source has similar n.m.r. and m.s. spectra and t.l.c. behaviour to the synthetic compound of Example 2.

EXAMPLE 2

Preparation of 6-Acetoxy-5-hexadecanolide (1A) 1-Bromoundecane

Undecanol (14 g), 48% aqueous hydrobromic acid (30 g) and concentrated sulphuric acid (5 ml) are heated together under reflux for 5½ hours. After cooling, water is added and the organic layer is separated, washed with concentrated sulphuric acid (20 ml), brine (50 ml) and dilute aqueous sodium carbonate (50 ml), and is then dried over calcium chloride. Distillaion under vacuum gives 1-bromoundecane (12 g) as a yellow oil, b.p. 60°–70° C./0.1 mm.

(1B) Ethyl 5-oxopentanoate

Ethyl 5-bromopentanoate (42 g), sodium bicarbonate (34 g) and pyridine N-oxide (38 g) in toluene (250 ml) are heated together under reflux in an atmosphere of nitrogen with vigorous stirring for 9 hours. After cooling, the product is partitioned with water (400 ml). The toluene layer is separated and the aqueous layer is extracted with a further amount of toluene (100 ml). The combined toluene extracts are dried over magnesium sulphate and the toluene removed by fractional distillation. The residue is distilled under vacuum to give ethyl 5-oxopentanoate as a colourless oil (14.1 g), m.s. M+144.

(2) (Z)-Hexadec-5-enoic Acid

Undecyltriphenylphosphonium bromide (16.3 g, prepared by heating 1-bromoundecane and triphenylphosphine together in refluxing xylene) is suspended in dry ether (400 ml) and the mixture is stirred under nitrogen whilst 1.7 M butyllithium in hexane (47.5 ml) is added from a syringe. The resulting bright red solution is cooled to 10° C. and treated dropwise with ethyl 5-oxopentanoate (7.25 g) in dry ether (50 ml). After 10 minutes, water (200 ml) is added and when the solid product has dissolved the ether layer is separated and the aqueous layer is washed with ether (3×100 ml). The combined ethereal solutions are dried over magnesium sulphate and the ether is evaporated. The residue is shaken with hexane (200 ml), and the mixture is cooled and filtered. The filtrate is concentrated to a volume of 100 ml and then cooled to allow crystallisation of the triphenylphosphine oxide. When this is complete, the mixture is filtered and the filtrate is evaporated to yield ethyl (Z)-hexadec-5-enoate in crude form as a yellow oil (10.1 g).

The above oil is mixed with 10% w/v aqueous sodium hydroxide solution (120 ml), tetrahydrofuran (120 ml) and methanol (120 ml) and the mixture is heated under reflux in an atmosphere of nitrogen for 45 minutes. After cooling and filtering, the filtrate is acidified to litmus with 14% w/v hydrochloric acid. The product is extracted with ether (2×100 ml), and the extract is dried (MgSO$_4$) and evaporated to yield (Z)-5-hexadecenoic acid as a straw coloured oil (6.8 g), m.s. M+254, $^{13}$C n.m.r. (CDCl$_3$/TMS) −26.6 (4C) and −27.3 (7C) p.p.m.

(3) dl-erythro-5,6-Dihydroxyhexadecanoic Acid (Z)-5-Hexadecenoic acid (6 g) is dissolved in 0.3 M aqueous potassium hydroxide (120 ml) and the stirred solution is cooled to 0° C. and treated with 0.5 M aqueous potassium permanganate (32 ml). The resulting product is centrifuged and the supernatant liquid is removed. The remaining residue is resuspended in 0.3 M aqueous potassium hydroxide (120 ml) and the product again centrifuged and the supernatant liquid removed. The combined supernatants are acidified with 25% v/v acetic acid and the resultant precipitate is filtered off and washed with ether to give dl-erythro-5,6-dihydroxyhexadecanoic acid as a white powder (1.5 g), m.p. 122°–123° C., $v_{max}$ (nujal) 1700cm$^{-1}$. On recrystallisation from ethanol traces of the threo isomer are removed to give pure dl-erythro-5,6-dihydroxyhexadecanoic acid as colourless crystals (190 mg from 200 mg), m.p. 125° C.

4(a) dl-erythro-6-Acetoxy-5-hexadecanolide dl-erythro-5,6-Dihydroxyhexadecanoic acid (4 mg) is treated with acetic anhydride (20 μl) in dry pyridine (50 μl) for 12 hours. Water (200 μl) is then added and the resultant mixture is extracted with ether (200 μl). After washing with water (3×200 μl) the ether extract is dried over magnesium sulphate and the ether is evaporated to give dl-erythro-6-acetoxy-5-hexadecanolide as a colourless oil (3 mg), δ($^1$H n.m.r. in CDCl$_3$/TMS) 0.88 (tr, CH$_3$), 1.26 (m, 8×CH$_2$), 1.69–2.00 (m, 3CH$_2$, 4CH$_2$ and 7CH$_2$), 2.08 (s, CH$_3$CO), 2.53 (m, CH$_2$CO), 4.35 (m, 6CH or 5CH), 4.98 (m, 5CH or 6CH); t.l.c. (silica gel 60, 0.25 mm, with ether) single spot of R$_f$0.39; g.c.m.s. (under conditions indicated in Example 1) single peak of R$_t$ 64 minutes with M+312 and other e.i. mass spectrum peaks including m269 (1.0%) and m252 (3.3%).

4(b) dl-erythro-6-Acetoxy-5-hexadecanolide dl-erythro-5,6-Dihydroxyhexadecanoic acid (2 g) is dissolved in acetyl chloride (7 ml) and the solution allowed to stand overnight at room temperature. Ether (30 ml) and water (30 ml) are then added with cooling. The organic phase is washed with water (30 ml), aqueous sodium bicarbonate (3×30 ml) and brine (30 ml), and then dried (MgSO$_4$. H$_2$O). The dried solution is evaporated to give dl-erythro-6-acetoxy-5-hexadecanolide as a straw coloured oil (1.5 mg) with physical properties identical to those of the product obtained under 4(a). NOTE: The compound dl-threo-6-acetoxy-5-hexadecanolide is prepared by an exactly similar procedure from (E)-hexadec-5-enoic acid. The properties of this compound differ in that it has an R$_t$ value on g.c.m.s. of 66 minutes and gives more intense ions at m269 (3.8%) and m252 (6.2%).

EXAMPLE 3

Preparation of dl-erythro-6-Acetoxy-5-dodecanolide

(1) (Z)-Dodec-5-enoic Acid

Heptyltriphenylphosphonium bromide (16.8g), prepared from 1-bromoheptane and triphenylphosphine analogously to undecyltriphenylphosphonium bromide as described in Example 2(2), is suspended in dry ether (300 ml) and the mixture is treated whilst stirring under nitrogen with 1.7 M butyllithium in hexane (36 ml) from a syringe. The resulting bright red solution is cooled to 10° C. and treated dropwise with ethyl 5-oxopentanoate [5.5 g, prepared as described in Example 2 (1B)] in dry ether (37.5 ml). After 10 minutes, the reaction mixture is worked up by the procedure described in Example 2(2) to give ethyl (Z)-dodec-5-enoate as a yellow oil (8.6g).

This oil is treated by the procedure described under Example 2(2) in order to effect hydrolysis and yield (Z)-dodec-5-enoic acid (3.5 g) as an oil (3.5 g).

(2) dl-erythro-5,6-Dihydroxydodecanoic acid (Z)-Dodec-5-enoic acid (3 g) is treated with aqueous KOH/KMnO$_4$ by the procedure described under Example 2(3) to yield dl-erythro-5,6-dihydroxydecanoic acid as a solid (0.2 g), m.p. 118° C.

(3) dl-erythro-6-Acetoxy-5-dodecanolide dl-erythro-5,6-Dihydroxydodecanoic acid (100 mg) is treated with acetyl chloride by the procedure described under Example 2(4b) to yield dl-erythro-6-acetoxy-5-dodecanolide as a colourless oil (78 mg), $^{13}$C n.m.r.

(CDCl$_3$/TMS) −170.9 (>C=O), −170.4 (>C=O), −80.5 (>CH—O—), −74.3 (>CH—O—) p.p.m.

EXAMPLE 4

Test of Oviposition Activity of dl-erythro-6-Acetoxy-5-hexadecanolide 0.1 ml of a solution in hexane of synthetic 6-acetoxy-5-hexadecanolide (7.5 μg, 25 egg raft equivalents) prepared as described in Example 2 was pipetted onto a 12 mm×1 mm polystyrene disc. The disc was allowed to dry by evaporation of the solvent and was then floated on the surface of 250 ml of tap water contained in a bowl of 13 cm diameter. 0.1 ml of hexane at the same temperature was pipetted similarly onto a control disc which was dried and then floated on the surface of 250 ml of tap water in a similar bowl. The two bowls were placed in a 30 cm×30 cm×30 cm cage containing *Culex pipiens fatigans* mosquitoes, females of which had fed earlier on an anaesthetized guinea pig. A sugar pad was placed between the two bowls and equidistant from them. The number of egg rafts laid in both the test bowl and the control bowl was counted next day following a 16 hour period of darkness.

The activity of the synthetic compound was compared with that of the natural egg rafts by means of similar experiment to that just described in which the two bowls instead contained, respectively, tap water and tap water on the surface of which floated from 7 to 25 *Culex pipiens fatigans* egg rafts.

The results of seven replicate experiments with the synthetic compound and the natural egg rafts are given in the Table, the positions of the test and control bowls in the cage being alternated with each replicate. It will be seen that in both cases the number of egg rafts laid in the test bowl substantially exceeded the number laid in the control bowl.

TABLE 1

| Number of egg rafts laid | | | |
|---|---|---|---|
| Synthetic Compound | | 7–25 Egg rafts | |
| Test bowl | Control bowl | Test bowl | Control bowl |
| 4 | 0 | 6 | 0 |
| 11 | 0 | 11 | 1 |
| 7 | 0 | 25 | 14 |
| 6 | 0 | 9 | 2 |
| 20 | 13 | 10 | 6 |
| 15 | 3 | 21 | 13 |
| 82 | 10 | 10 | 6 |
| Total 145 | 26 | 92 | 42 |

EXAMPLE 5

Test of Oviposition Activity of dl-erythro-6-Acetoxy-5-hexadecanolide

The same procedure as described in Example 4 was used to compare with a control the activity as observed for either 10 or 11 replicates of synthetic 6-acetoxy-5-hexadecanolide, prepared as described in Example 2, over a wide range of concentration from 0.01 μg up to 7.5 μg. The results obtained at each concentration, as a total for the 10 or 11 replicates of the experiment and the same number of the control, are shown in Table 2 from which it will be seen that a statistically significant attractant effect was present over the range 0.02–7.5 μg and that there was no evidence of a changeover to repellancy at the higher concentrations.

In a second experiment a direct comparison was made between the attractancy at a concentration of 7.5 μg of thee synthetic and the natural 6-acetoxy-5-hexadecanolide. This was done by using a pair of bowls in one of which the floating disc contained the synthetic compound prepared as described in Example 2 and the other of which contained the naturally occurring compound isolated as described in Example 1. Totalled for ten replicates, a similar level of attraction was observed (synthetic: 74 egg rafts; natural: 82 egg rafts; t=0.357, p>0.7).

TABLE 2

| Attractant activity over range of concentration | | | |
|---|---|---|---|
| Concentration μg | Number of egg rafts in test bowl and (% of total number) | Number of egg rafts in control bowl | Student t, probability |
| 7.5 | 209 (85) | 37 | t = 2.337 p < 0.05 |
| 3.7 | 129 (81) | 31 | t = 3.419 p < 0.01 |
| 3.0 | 101 (80) | 25 | t = 6.039 p < 0.001 |
| 0.3 | 126 (80) | 31 | t = 2.319 p < 0.05 |
| 0.08 | 159 (84) | 31 | t = 4.571 p < 0.01 |
| 0.02 | 169 (71) | 70 | t = 2.628 p < 0.05 |
| 0.01 | 83 (54) | 70 | t = 0.750 p > 0.4 |

We claim:

1. A method for mosquito control which comprises attracting mosquitos by applying to a location an effective mosquito attractant amount of a compound of the formula (I)

in which R is formyl or alkanoyl of two to ten carbon atoms and R' is alkyl of six to twelve carbon atoms.

2. A method according to claim 1, in which R' is alkyl of eight to ten carbon atoms.

3. A method according to claim 2, in which R' is n-octyl or n-decyl.

4. A method according to claim 1, in which R is formyl or alkanoyl of two to five carbon atoms.

5. A method according to claim 4, in which R is formyl, acetyl or propionyl.

6. A method according to claim 5, in which R is acetyl.

7. A method according to claim 1, in which the compound is 6-acetoxy-5-tetradecanolide.

8. A method according to claim 1, in which the compound is 6-acetoxy-5-hexadecanolide.

9. A method according to claim 1, in which the compound is in the erythro configuration.

10. A method according to claim 2, in which R is formyl or alkanoyl of two to five carbon atoms.

11. A method according to claim 2, in which R is formyl, acetyl or propionyl.

12. A method according to claim 2, in which R is acetyl.

13. A method according to claim 3, in which R is formyl or alkanoyl of two to five carbon atoms.

14. A method according to claim 3, in which R is formyl, acetyl or propionyl.

15. A method according to claim 7, in which the compound is in the erythro configuration.

16. A method according to claim 8, in which the compound is in the erythro configuration.

17. A method according to claim 1, wherein an effective amount of an insecticide is applied to said location.

18. A method according to claim 17, wherein mosquito eggs and/or larvae are destroyed.

19. A mosquito attracting composition which comprises an effective mosquito attractant amount of a compound of the formula (I)

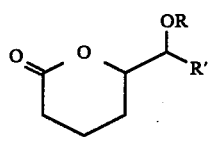

in which R is formyl or alkanoyl of two to ten carbon atoms and R' is alkyl of six to twelve carbon atoms, in combination with a suitable carrier.

20. A composition according to claim 19, in which R' is alkyl of eight to ten carbon atoms.

21. A composition according to claim 20, in which R' is n-octyl or n-decyl.

22. A composition according to claim 19, in which R is formyl or alkanoyl of two to five carbon atoms.

23. A composition according to claim 22, in which R is formyl, acetyl or propionyl.

24. A composition according to claim 23, in which R is acetyl.

25. A composition according to claim 19, in which the compound is 6-acetoxy-5-tetradecanolide.

26. A composition according to claim 19, in which the compound is 6-acetoxy-5-hexadecanolide.

27. A composition according to claim 19, in which the compound is in the erythro configuration.

28. A composition according to claim 20, in which R is formyl or alkanoyl of two to five carbon atoms.

29. A composition according to claim 20, in which R is formyl, acetyl or propionyl.

30. A composition according to claim 20, in which R is acetyl.

31. A composition according to claim 21, in which R is formyl or alkanoyl of two to five carbon atoms.

32. A composition according to claim 21, in which R is formyl, acetyl or propionyl.

33. A composition according to claim 25, in which the compound is in the erythro configuration.

34. A composition according to claim 26, in which the compound is in the erythro configuration.

35. A composition according to claim 19, which further contains an insecticidally effective amount of an insecticide.

* * * * *